United States Patent [19]
Atlee, III

[11] Patent Number: 5,394,880
[45] Date of Patent: Mar. 7, 1995

[54] ESOPHAGEAL STETHOSCOPE

[76] Inventor: John L. Atlee, III, N71 W29436 Tamron La., Hartland, Wis. 53029

[21] Appl. No.: 210,001

[22] Filed: Mar. 17, 1994

[51] Int. Cl.⁶ ............................................. A61B 5/02
[52] U.S. Cl. .................................... 128/715; 607/124
[58] Field of Search .............. 607/119, 122, 123, 124; 128/642, 661.08, 668, 695, 696, 697, 701, 715, 724, 773

[56] References Cited

U.S. PATENT DOCUMENTS

| | | | |
|---|---|---|---|
| Re. 31,377 | 9/1983 | Mylrea et al. | 128/642 |
| 1,207,479 | 12/1916 | Bisgaard | 604/104 |
| 3,690,769 | 9/1972 | Mori | 356/41 |
| 3,847,483 | 11/1974 | Shaw et al. | 356/41 |
| 3,951,136 | 4/1976 | Wall | 128/2.06 E |
| 4,090,518 | 5/1978 | Elam | 128/349 |
| 4,114,604 | 9/1978 | Shaw et al. | 128/2 L |
| 4,176,660 | 12/1979 | Mylrea et al. | 128/671 |
| 4,301,809 | 11/1981 | Pinchak | 128/695 |
| 4,475,555 | 10/1984 | Linder | 128/670 |
| 4,476,872 | 10/1984 | Perlin | 128/642 |
| 4,484,583 | 11/1984 | Graham | 128/671 |
| 4,623,248 | 11/1986 | Sperinde | 356/41 |
| 4,640,298 | 2/1987 | Pless et al. | 128/784 |
| 4,706,688 | 11/1987 | Don Michael et al. | 128/785 |
| 4,714,080 | 12/1987 | Edgar, Jr. et al. | 128/633 |
| 4,960,133 | 10/1990 | Hewson | 128/784 |
| 4,981,470 | 1/1991 | Bombeck, IV | 128/635 |
| 5,036,848 | 8/1991 | Hewson | 128/419 |
| 5,052,390 | 10/1991 | Hewson | 128/419 |
| 5,154,387 | 10/1992 | Trailer | 128/784 |
| 5,170,803 | 12/1992 | Hewson et al. | 128/786 |
| 5,178,149 | 1/1993 | Imburgia et al. | 128/662.06 |
| 5,179,952 | 1/1993 | Buinevicius et al. | 128/642 |
| 5,191,892 | 3/1993 | Blikken | 128/715 |

OTHER PUBLICATIONS

Christine Z. Pattison, M.D., et al., "Atrial Pacing Thresholds Measured in Anesthetized Patients with the Use of an Esophageal Stethoscope Modified for Pacing", *Anesthesiology*, vol. 74, No. 5, May, 1991, pp. 854–859.

H. R. Andersen, et al., "Trans-Esophageal Pacing", *PACE*, vol. 6, Jul.-Aug. 1983, pp. 674–679.

*Primary Examiner*—William E. Kamm
*Assistant Examiner*—Marianne H. Parker
*Attorney, Agent, or Firm*—Michael, Best & Friedrich

[57] ABSTRACT

An esophageal stethoscope comprises a tubular flexible body having a proximal end and a closed distal end, an acoustic region defined on the body and spaced from the closed distal end. First and second spaced apart electrodes are mounted on one side of the body and between the distal end and the acoustic input region. The electrodes are spaced from each other and the distance between the mid-point of the electrodes and the acoustic input region is about 5–10 cm. A second pair of electrodes are mounted between the distal end and the first electrode pair and are manually movable laterally into engagement with the esophageal tissue.

19 Claims, 1 Drawing Sheet

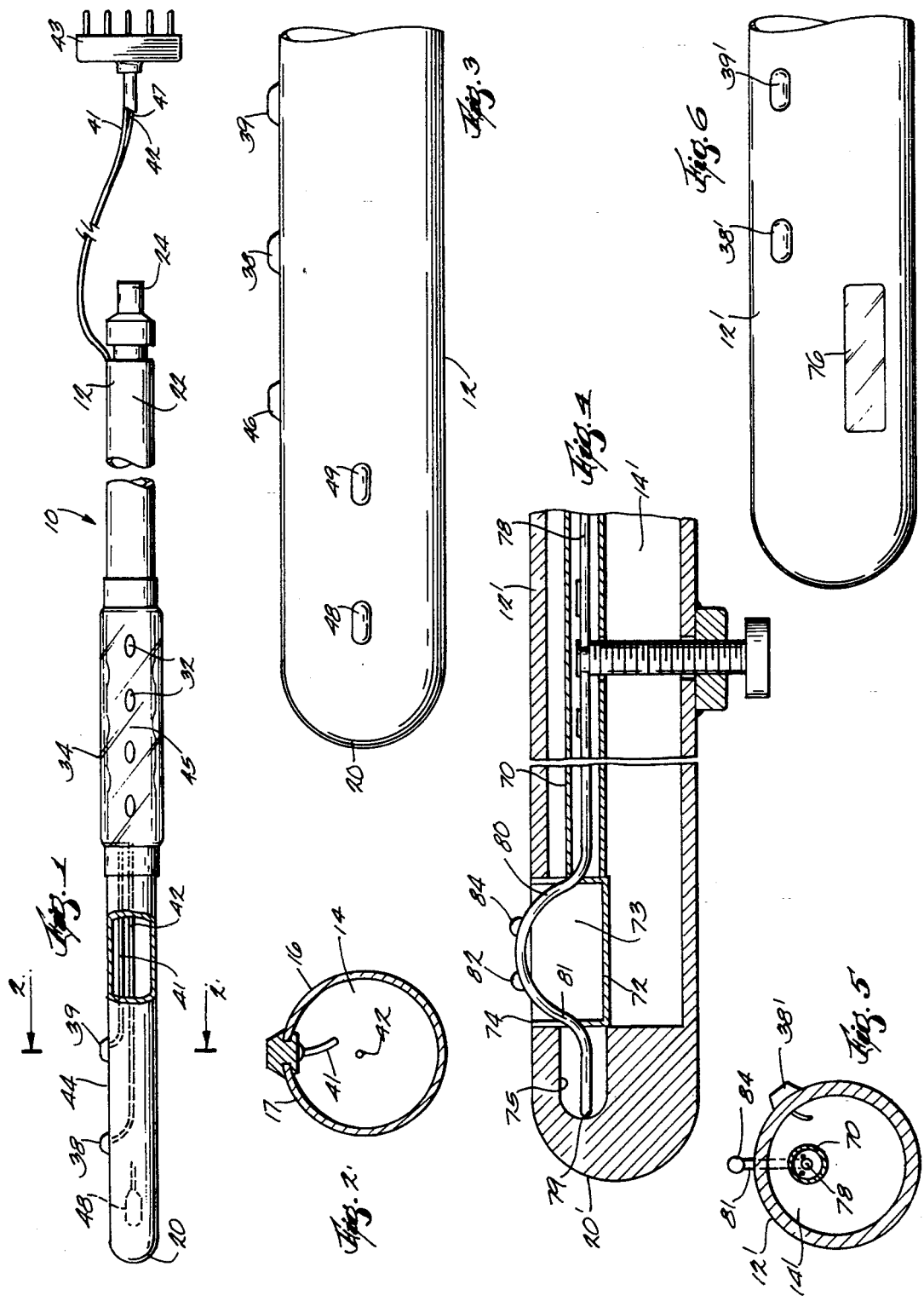

ESOPHAGEAL STETHOSCOPE

BACKGROUND OF THE INVENTION

This invention relates to esophageal probes, and more particularly, to an esophageal probe for performing transesophageal atrial and ventricular pacing and electrocardiographic (ECG) recording and monitoring.

Esophageal catheters for performing various functions are well known in the art. These include catheters for cardiac pacing or recording as disclosed, for example, in U.S. Pat. Nos. 4,937,521 and 5,154,387. Another type of catheter is an esophageal stethoscope which includes a diaphragm for listening to heart and breath sounds. Most esophageal stethoscopes also incorporate thermistor sensors for monitoring core body temperature. The thermistor is positioned at the distal end of the esophageal stethoscope, just beyond the distal margin of the acoustic diaphragm. When prior art esophageal stethoscopes are in a position to best discern breath sounds, the thermistor measurement is affected by the movement of relatively cold gases which are inspired during mechanical or artificial respiration. In one prior art esophageal stethoscope, the thermistors are positioned approximately 7 cm distal to the distal margin of the acoustic diaphragm.

Prior art thermistor equipped esophageal stethoscopes capable of ECG recording and/or cardiac pacing generally include bipolar electrodes that are located proximal to the acoustic diaphragm. This configuration has been found to be undesirable because heart sounds are best heard with the electrode center point withdrawn 5 cm, and breath sounds are best heard with the electrode center point 10 cm from the point of minimum pacing thresholds. Thus, the pacing and recording electrodes in prior art esophageal stethoscopes are not correctly positioned relative to the acoustic diaphragm.

Pacing and recording electrodes of prior art esophageal stethoscopes generally comprise a band or ring of conductive material which surrounds the probe. These have been found to be unsatisfactory because they tend to become dislodged, i.e. slip along the tubular barrel assembly thereby exposing bare wire connectors that could damage tissue lining the esophagus. In addition, when band or ring electrodes are used for cardiac pacing they have high current requirements due to current dispersion.

SUMMARY OF THE INVENTION

It is an object of the invention to provide a new and improved esophageal stethoscope.

Another object of the invention is to provide an esophageal stethoscope having a temperature sensor which is positioned to more accurately reflect body temperature.

A further object of the invention is to provide an esophageal stethoscope which permits heart and breath sounds to be heard during pacing or ECG recording or monitoring.

Yet another object of the invention is to provide an esophageal probe which can be used for both atrial and ventricular pacing.

A still further object of the invention is to provide an esophageal probe having electrodes for cardiac pacing or recording which are not prone to dislodgement.

It is another object of the invention to provide an esophageal probe having electrodes for cardiac pacing or recording which have relatively low current requirements.

Still another object of the invention is to provide an esophageal probe having atrial pacing electrodes with means for ventricular pacing during emergencies and while the probe is already positioned in the esophagus.

These and other objects and advantages of the present will become more apparent from the detailed description thereof taken with the accompanying drawings.

In general terms the invention comprises an esophageal stethoscope comprising a tubular flexible body having a proximal end and a closed distal end, an acoustic region defined on the body and spaced from the closed distal end, first and second spaced apart electrodes mounted on one side of the body and between the distal end and the input region, the electrodes being spaced from each other and the distance between the mid-point of the electrodes and the acoustic input region being about 5-10 cm. According to another aspect of the invention third and fourth electrodes are disposed on said one side of the body and between the distal end thereof and the first and second electrodes and being movable laterally relative to the body and are engageable with the esophageal tissue.

BRIEF DESCRIPTION OF THE DRAWINGS

FIG. 1 is a side view with parts broken away of an esophageal stethoscope in accordance with the invention;

FIG. 2 is a view taken along lines 2—2 of FIG. 1;

FIG. 3 illustrates a first alternate embodiment of the invention;

FIG. 4 is a side view, with parts broken away of a second alternate embodiment of the invention;

FIG. 5 is a view taken along lines 5—5 of FIG. 4; and

FIG. 6 is a top view of a portion of the esophageal probe shown in FIG. 4.

DETAILED DESCRIPTION OF THE PREFERRED EMBODIMENT

FIGS. 1 and 2 illustrate an esophageal stethoscope 10 in accordance with the preferred embodiment of the invention. The stethoscope 10 includes a flexible, elongated tubular barrel 12 having an internal lumen 14, and a wall 16 of a predetermined thickness and having an outer surface 17. The barrel 12 has a distal end 20 and a proximal end 22 which may, for example, terminate in a standard luer acoustic adapter 24 that may be coupled to conventional molded ear pieces or a stethoscope. The distal end 20 of the barrel 12 is generally hemispherically shaped and may be formed, for example, as a silicone plug which is attached to the distal end of the catheter to facilitate insertion.

Spaced proximally of the distal end 20 is an acoustic input 30 or a microphone sensor element. The acoustic input 30 has a plurality of openings 32 in the peripheral wall 16. The openings 32 can be symmetrically spaced around the barrel 12, and all are covered by a thin membrane 34 which transmits cardiac and respiration sounds. The membrane 34 is sealed to the catheter 10 at the opposite ends of the input section 30 to cover the openings 32 and prevent the entry of fluids into the barrel 12. The acoustic input is connected by the lumen 14 to the adapter 24.

A pair of electrodes 38 and 39 are mounted on the outer wall 16 of the barrel 12 between the distal end 26 and the acoustic input 30 and each preferably projects upwardly from the outer surface 17. The electrodes 38 and 39 are preferably formed of stainless steel and are spaced from each other and from the distal end 26 and the acoustic input 30. The electrodes 38 and 39 are coupled by conductors 41 and 42 extending through the lumen 14 to respectively connect electrodes 38 and 39 to end connector 43 at the proximal end. The electrodes 38 and 39 may be used for atrial or ventricular ECG monitoring or recording or atrial pacing. Connector 43 is adapted to be coupled through a cable (not shown) to the appropriate recording, monitoring or pacing apparatus.

I have found that if the practitioner wishes to receive maximal input of heart and breath sounds while performing transesophageal atrial pacing or ECG recording or monitoring, the center point 44 of the electrodes 38 and 39 must be 5–10 cm from the center point 45 of the acoustic input 30. Heart sounds are best heard at 5 cm and breath sounds at 10 cm. While breath sounds are not optimal at 5 cm, heart sounds can be heard relatively well at 10 cm. Accordingly, a compromise of about 8 cm produces acceptable breath and heart sounds.

A temperature sensing element or thermistor 46 is disposed adjacent the distal end of the esophageal stethoscope lumen so that cold inspired gases within the tracheobronchial tree have minimum effect to lower core body temperature measurements. The thermistor element 46 should be positioned so as not to interfere with trans-esophageal pacing or recording functions and vice versa. The element is preferably positioned 1–2 cm distal to the distal electrode 38 of the esophageal electrode pair and resides within the esophageal lumen. Alternately, the thermistor element 46 could reside along the outer surface of the stethoscope barrel 12, so long as it is at least 5 cm distal to the inferior margin of the acoustic input region 30. Thermistor 46 is connected by conductors 47 to connector 43 so that it may be connected to an external monitor.

The projecting electrodes 38 and 39 are fixed to the wall of the barrel to prevent movement along the barrel surface as sometimes occurs with prior art ring electrodes. Moreover, the projecting electrodes reduce current dispersion and lower energy requirements. In the preferred embodiment, the electrodes 38 and 39 have a surface area of 0.5–1.0 cm and project about 3–6 mm from the barrel assembly. This will maximize electrode contact with the esophageal wall and reduce the esophageal-left atrial distance so that the current needed for atrial pacing is reduced.

If the practitioner desires to perform ventricular recording during atrial pacing, a second pair of electrodes are required. A pair of transesophageal ventricular electrodes 48 and 49 are shown in FIG. 3. Preferably, for adults and the center point 50 of the ventricular electrodes 48 and 49 is about 4–5 cm distal relative to the center point 44 of atrial electrodes 38 and 39. In addition, the electrodes 48 and 49 are offset about 30°–45° counterclockwise from the electrodes 38 and 39.

I have found that the best position for recording a maximum deflection ventricular ECG complex (Vmax) from the esophagus is 4–5 cm distal from the best atrial ECG complex (Pmax). The Vmax point is also the best position for sustained ventricular pacing capture when using probes with inter-electrode distances of 2.0, 5.5 or 7.5 cm, provided the electrodes closest to Vmax serves as the cathode. Therefore, the center point 50 of the recording electrodes should be 8–12 cm distal to the distal or inferior margin of the acoustic diaphragm or microphone sensor element 30. In addition, the thermistor element 46 should be positioned at least 7 cm distal to the diaphragm; or, approximately midway between the atrial and ventricle electrode pair center points. The thermistor element may project one to several millimeters from the barrel assembly of the esophageal stethoscope to contact esophageal mucosal tissue.

Atrial pacing alone is sufficient to meet the majority of temporary pacing needs, especially in anesthesiology and most intensive care unit settings. However, transesophageal pacing probes having electrodes for atrial pacing might be justified for emergency rooms, coronary care units and rescue operations, where there is a higher incidents of advanced AV heart block.

FIGS. 4–6 show a further embodiment of the invention to comprise a pacing esophageal stethoscope having electrodes for atrial pacing with a means for introducing ventricular pacing electrodes when necessary. This embodiment of the invention includes an esophageal stethoscope which includes a barrel 12' having a lumen 14'. In addition, a second lumen 70 is provided within the lumen 14' and extends through the proximal end. Adjacent the distal end of the barrel 12' there is a narrow guide 72 and is sealed from the lumen 14' and communicates with the lumen 70. The housing 72 is defined by an enclosure 73 which is open at its upper end 74. The end of the enclosure 73 also communicates with an enclosure 75 formed in the distal end 20. A thin membrane 76 overlaps the opening 74 which normally seals the enclosure 73.

In operation, the electrodes 38' and 39' are used for atrial pacing. If it is determined that ventricular pacing is required, an electrode carrier 78 would be inserted into the lumen 70. The carrier 78 consists of a thin wire having a blunted end 79 and spaced flex points 80 and 81 adjacent its distal end. At least two spaced apart electrodes 82 and 84 are disposed on one side of the carrier 78 between the flex points 80 and 81. When ventricular pacing is required the carrier 78 and the wire 80 are inserted through the proximal end of body 121 into the linmen 70. When the end 79 of the carrier 78 passes through the guide 72 and engages the receptacle 83, the carrier 78 will flex as shown in FIG. 4 thereby causing the end to bow outwardly to move the electrodes 82 and 84 laterally as the carrier is guided by the sidewalls of the guide 72, through the membrane 76 and into contact with the wall of the esophagus. This action also displaces the wall of the esophagus so that the electrodes 82 and 84 move to within about 1 cm of the posterior left ventricle. As a result, the ventricular pacing threshold is reduced below about 20 to 25 ma for pulsterations equal to or less than about 12 Msec with an assumed esophageal mucosa resistance equal to or less than about 1,000 ohms. The ventricular electrode center to center distance should be about 1.3–2 cm. Because the wire 79 extends from the proximal end of the lumen 70, it can be manipulated and fixed in position after the Carrier 78 has flexed.

The amount of lateral displacement of electrodes 82 and 84 are controlled by the operator. Markings on the proximal end of the carrier 78 indicates how far the electrodes have been advanced and means, such as a clamp or thumb screw (not shown), are preferably provided to clamp the carrier and thereby retain the electrodes in their advanced position.

While only a few embodiments of the invention have been illustrated and described, it is not intended to be limited thereby but only by the scope of the appended claims.

I claim:

1. An esophageal stethoscope comprising a tubular flexible body having a proximal end and a closed distal end, an acoustic input region defined on said body and spaced from said closed distal end, first and second spaced apart electrodes mounted on said body and between said distal end and said acoustic input region, said electrodes being spaced from each other and the acoustic input region, the distance between the mid-point of the space between said electrodes and said acoustic input region being about 5–10 cm.

2. The esophageal stethoscope set forth in claim 1 wherein the distance between the mid-point of the electrodes and the acoustic input region being about 8 cm.

3. The esophageal stethoscope set forth in claim 1 and further including third and fourth electrodes disposed on said body and between the distal end of said body and the first and second electrodes.

4. The esophageal stethoscope set forth in claim 3 wherein said third and fourth electrodes are offset from the first pair of electrodes through a rotational angle of about 38°–45°.

5. The esophageal stethoscope set forth in claim 4 and including a carrier disposed within said body, said third and fourth electrodes being mounted on said carrier, and means coupled to said carrier for manipulating said carrier from the proximal end of said body for moving the third and fourth electrodes laterally relative to the body.

6. The esophageal stethoscope set forth in claim 1 wherein said body has an outer surface, said first and second electrodes project about 3–6 mm from the outer surface of the body.

7. The esophageal stethoscope set forth in claim 1 wherein said first and second electrodes each has a center point, the distance between the center point of the first electrode and the center point of the second electrode is about 4 cm.

8. The esophageal stethoscope set forth in claim 1 wherein the body defines an interior audio lumen, and a second lumen extending through said first lumen, an opening adjacent the distal end of the body, a guide coupled to said port and communicating with said second lumen, and a flexible carrier constructed within the second lumen and having a flexible end, at least a pair of electrodes mounted on said flexible end wherein insertion of said carrier into said second lumen will flex the end of said carrier outwardly to move said electrodes laterally through said opening.

9. The esophageal stethoscope set forth in claim 1 wherein said acoustic input region has proximal and distal ends, and including a temperature sensor disposed adjacent the distal end of said body and about 7 cm distal to the distal end of the acoustic input region.

10. The esophageal stethoscope set forth in claim 1 wherein body has an axis, said electrodes being disposed on one side of a plane containing said axis said electrodes extending outwardly from the surface of said body.

11. The esophageal stethoscope set forth in claim 1 wherein there are at least third and forth electrodes located on said body and spaced distally from said first and second electrodes.

12. The esophageal stethoscope set forth in claim 11 wherein said third and fourth electrodes are offset from the first and second electrodes through a rotational angle of about 30°–45°.

13. The esophageal stethoscope set forth in claim 12 wherein the distance between a first point midway between said first and second electrodes and a second point midway between said third and fourth electrodes is about 4 cm.

14. An esophageal probe comprising a tubular flexible body having a proximal end and a closed distal end, first and second spaced apart electrodes mounted on said body and adjacent said distal end, said electrodes being spaced from each other longitudinally on said body, and at least two additional electrodes disposed on said body and between the distal end of said body and the first and second electrodes.

15. The esophageal probe set forth in claim 14 wherein said tubular body has an axis, said at least two additional electrodes being offset from the first and second electrodes through a rotational angle of about 300–400 relative to said axis.

16. The esophageal stethoscope set forth in claim 14 wherein said body has an outer surface, said first and second electrodes projecting about 3-6 mm from said outer surface.

17. The esophageal probe set forth in claim 14 and including a carrier disposed within said body, said additional electrodes being mounted on said carrier and means coupled to said carrier for manipulating said carrier from the proximal end of said body for moving said third and fourth electrodes laterally relative to the body.

18. The esophageal stethoscope set forth in claim 14 wherein the distance between a first point midway between said first and second electrodes and a second point midway between said additional electrodes is about 4 cm.

19. The esophageal stethoscope set forth in claim 18 wherein the body defines an interior audio lumen, and second lumen extending through said first lumen, an opening adjacent the distal end of the body, a guide coupled to said port and communicating with said second lumen, a flexible carrier disposed within said second lumen and extending into said guide, said additional electrodes being mounted on said carrier and disposed within said guide, said carrier extending from the proximal end of the body, whereby manipulation of the carrier flexes that portion of the carrier within said guide to move said additional electrodes outwardly through said opening.

* * * * *